United States Patent
Flask et al.

(10) Patent No.: US 11,442,127 B2
(45) Date of Patent: Sep. 13, 2022

(54) SYSTEM AND METHOD FOR DYNAMIC MULTIPLE CONTRAST ENHANCED, MAGNETIC RESONANCE FINGERPRINTING (DMCE-MRF)

(71) Applicant: Case Western Reserve University, Cleveland, OH (US)

(72) Inventors: Chris Flask, Cleveland, OH (US); Christian Anderson, Cleveland, OH (US); Xin Yu, Cleveland, OH (US); Nicole Steinmetz, Cleveland, OH (US); Mark A. Griswold, Cleveland, OH (US); Susann Brady-Kalnay, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 248 days.

(21) Appl. No.: 16/603,335

(22) PCT Filed: Apr. 6, 2018

(86) PCT No.: PCT/US2018/026580
§ 371 (c)(1),
(2) Date: Oct. 7, 2019

(87) PCT Pub. No.: WO2018/187760
PCT Pub. Date: Oct. 11, 2018

(65) Prior Publication Data
US 2020/0041595 A1 Feb. 6, 2020

Related U.S. Application Data

(60) Provisional application No. 62/482,755, filed on Apr. 7, 2017.

(51) Int. Cl.
*G01R 33/50* (2006.01)
*A61B 5/055* (2006.01)
(Continued)

(52) U.S. Cl.
CPC .............. *G01R 33/50* (2013.01); *A61B 5/055* (2013.01); *G01R 33/4828* (2013.01);
(Continued)

(58) Field of Classification Search
CPC ................ G01R 33/50; G01R 33/4828; G01R 33/5601; G01R 33/5602; G01R 33/5608;
(Continued)

(56) References Cited

U.S. PATENT DOCUMENTS 8,723,518 B2 5/2014 Seiberlich
2012/0262165 A1 10/2012 Griswold
(Continued)

OTHER PUBLICATIONS

Abakumova, T. et al. Connexin 43-targeted T1 contrast agent for MRI diagnosis of glioma. Contrast Media Mol. Imaging 11, 15-23 (2016).
(Continued)

*Primary Examiner* — Rishi R Patel
(74) *Attorney, Agent, or Firm* — Quarles & Brady LLP

(57) ABSTRACT

The present disclosure provides a method of DDCE-MRF. The method can include: a) introducing two or more contrast agents to a region of interest (ROI) of a subject, the two or more contrast agents having different relaxivities; b) measuring a T1 relaxation time and a T2 relaxation time for locations within the ROI using magnetic resonance fingerprinting (MRF); c) determining, using equations that relate the different relaxivities, the T1 relaxation time, the T2 relaxation time, and concentrations of the two or more contrast agents, the concentrations of the two or more contrast agents for each of the locations within the ROI; and d) producing an image depicting the ROI based, at least in part, on the concentrations of the two or more contrast agents.

8 Claims, 5 Drawing Sheets

(51) Int. Cl.
*G01R 33/56* (2006.01)
*G06T 7/00* (2017.01)
*G01R 33/48* (2006.01)

(52) U.S. Cl.
CPC ..... *G01R 33/5601* (2013.01); *G01R 33/5602* (2013.01); *G01R 33/5608* (2013.01); *G06T 7/0016* (2013.01); *G06T 2207/10096* (2013.01)

(58) Field of Classification Search
CPC ..... G01R 33/5635; A61B 5/055; A61B 5/113; A61B 5/7207; A61B 5/7289; G06T 7/0016; G06T 2207/10096; G06T 2207/30016; A61K 49/101
See application file for complete search history.

(56) References Cited

U.S. PATENT DOCUMENTS

| 2014/0292328 | A1* | 10/2014 | Brady-Kalnay ... | G01R 33/4822 324/309 |
| 2015/0173847 | A1* | 6/2015 | Hayashi ........... | A61B 6/037 600/431 |
| 2015/0301141 | A1 | 10/2015 | Griswold | |
| 2015/0301142 | A1 | 10/2015 | Griswold | |
| 2016/0270687 | A1 | 9/2016 | Brady-Kalnay | |

OTHER PUBLICATIONS

Ali, M. M., et al. Using two chemical exchange saturation transfer magnetic resonance imaging contrast agents for molecular imaging studies. Acc. Chem. Res. 42, 915-924 (2009).
Assländer, J., et al. Pseudo steady-state free precession for MR-Fingerprinting. Magn. Reson. Med. 77, 1151-1161 (2016).
Beg, M. S., et al. Porous Fe3O4-SiO2 core-shell nanorods as high-performance MRI contrast agent and drug delivery vehicle. J. Magn. Magn. Mater. 428, 340-347 (2017).
Bock, J. et al. 4D phase contrast MRI at 3 T: effect of standard and blood-pool contrast agents on SNR, PC-MRA, and blood flow visualization. Magn. Reson. Med. 63, 330-338 (2010).
Buonincontri, G. et al. MR fingerprinting with simultaneous B1 estimation. Magn. Reson. Med. 76, 1127-1135 (2016).
Caravan, P., et al. "Influence of molecular parameters and increasing magnetic field strength on relaxivity of gadolinium-and manganese-based T1 contrast agents." Contrast media & molecular imaging 4.2 (2009): 89-100.
Catanzaro, V. et al. A R2p/R1p ratiometric procedure to assess matrix metalloproteinase-2 activity by magnetic resonance imaging. Angew. Chemie—Int. Ed. 52, 3926-3930 (2013).
Cauley, S. F. et al. Fast group matching for MR fingerprinting reconstruction. Magn. Reson. Med. 74, 523-528 (2014).
Cloos, M. A. et al. Multiparametric imaging with heterogeneous radiofrequency fields. Nat. Commun. 7, 12445; doi:10.1038/ncomms12445 (2016).
Deoni, S. C. L., et al. High-resolution T1 and T2 mapping of the brain in a clinically acceptable time with DESPOT1 and DESPOT2. Magn. Reson. Med. 53, 237-241 (2005).
Dula, A. N., et al. Multiexponential T2, magnetization transfer, and quantitative histology in white matter tracts of rat spinal cord. Magn. Reson. Med. 63, 902-909 (2010).
Fernández-Cuervo, G., et al. A catalyCEST MRI contrast agent that can simultaneously detect two enzyme activities. ChemBioChem 17, 383-387 (2016).
Fuchs, B. C. et al. Molecular MRI of collagen to diagnose and stage liver fibrosis. J. Hepatol. 59, 992-998 (2013).
Gale, E. M., et al. A Janus chelator enables biochemically responsive MRI contrast with exceptional dynamic range. J. Am. Chem. Soc. 138, 15861-15864 (2016).
Gao, Y. et al. Preclinical MR fingerprinting (MRF) at 7 T: effective quantitative imaging for rodent disease models. NMR Biomed. 28, 384-394 (2015).

Hamilton, J. I. et al. MR fingerprinting for rapid quantification of myocardial T1, T2, and proton spin density. Magn. Reson. Med. 77, 1446-1459 (2016).
Herborn, C. U. et al. Comprehensive time-resolved MRI of peripheral vascular malformations. Am. J. Roentgenol. 181, 729-735 (2003).
Herrmann, K. et al. Dynamic quantitative T1 mapping in orthotopic brain tumor xenografts. Transl. Oncol. 9, 147-154 (2016).
Hiller, K.-H., et al. Assessment of cardiovascular apoptosis in the isolated rat heart by magnetic resonance molecular imaging. Mol. Imaging 5, 115-121 (2006).
Hingorani, D. V. et al. A single diamagnetic catalyCEST MRI contrast agent that detects cathepsin B enzyme activity by using a ratio of two CEST signals. Contrast Media Mol. Imaging 11, 130-138 (2016).
Hung, A. H., et al. Magnetic barcode imaging for contrast agents. Magn. Reson. Med. 77, 970-978 (2017).
Ingrisch, M. et al. Quantification of perfusion and permeability in multiple sclerosis. Invest. Radiol. 47, 252-258 (2012).
International Searching Authority, International Search Report and Written Opinion for application PCT/US2018/026580, dated Jun. 28, 2018, 9 pages.
Jiang, Y., et al. MR fingerprinting using fast imaging with steady state precession (FISP) with spiral readout. Magn. Reson. Med. 74, 1621-1631 (2015).
Kim, K. S., et al. A cancer-recognizable MRI contrast agents using pH-responsive polymeric micelle. Biomaterials 35, 337-343 (2014).
Kircher, M. F. et al. A brain tumor molecular imaging stralegy using a new triple-modality MRI-photoacoustic-Raman nanoparticle. Nat. Med. 18, 829-834 (2012).
Kitagawa, T. et al. RGD targeting of human ferritin iron-oxide nanoparticles enhances in vivo molecular MRI of experimental aortic aneurysms. J. Magn. Reson. Imaging 45, 1144-1153 (2016).
Kubaska, S., et al. Dual contrast enhanced magnetic resonance imaging of the liver with superparamagnetic iron oxide followed by gadolinium for lesion detection and characterization. Clin. Radiol. 56, 410-415 (2001).
Lauffer, R. B. Paramagnetic metal complexes as water proton relaxation agents for NMR imaging: theory and design. Chem. Rev. 87, 901-927 (1987).
Li, T. et al. A new interleukin-13 amino-coated gadolinium metallofullerene nanoparticle for targeted MRI detection of glioblastoma tumor cells. J. Am. Chem. Soc. 137, 7881-7888 (2015).
Lima, J. A. C. et al. Regional heterogeneity of human myocardial infarcts demonstrated by contrast-enhanced MRI. Circulation 92, 1117-1125 (1995).
Liu, X. et al. MRI contrast agent for targeting glioma: interleukin-13 labeled liposome encapsulating gadolinium-DTPA. Neuro. Oncol. 18, 691-699 (2016).
Ma D, et al., "Magnetic Resonance Fingerprinting," Nature, 2013; 495(7440):187-192.
Ma, D. et al. Slice profile and B1 corrections in 2D magnetic resonance fingerprinting. Magn. Reson. Med.; doi:10.1002/mrm. 26580 (2017).
Majumdar, S., et al. Quantitation of MR relaxation effects of iron oxide particles in liver and spleen. Radiology 169, 653-658 (1988).
Nofiele, J. T. et al. Ultrashort echo time for improved positive-contrast manganese-enhanced MRI of cancer. PLoS One 8, e58617; doi:10.1371/journal.pone.0058617 (2013).
Padhani, A. R. et al. Dynamic contrast enhanced MRI of prostate cancer: correlation with morphology and tumour stage, histological grade and PSA. Clin. Radiol. 55, 99-109 (2000).
Pu, F. et al. Prostate-specific membrane antigen targeted protein contrast agents for molecular imaging of prostate cancer by MRI. Nanoscale 8, 12668; 10.1053/crad.1999.0327 (2016).
Reimer, P., et al. Hepatobiliary contrast agents for contrast-enhanced MRI of the liver: properties, clinical development and applications. Eur. Radiol. 14, 559-578 (2004).
Rohrer, M., et al. Comparison of magnetic properties of MRI contrast media solutions at different magnetic field strengths. Invest. Radiol. 40, 715-724 (2005).
Schmitt, P. et al. Inversion recovery TrueFISP: quantification of T1, T2, and spin density. Magn. Reson. Med. 51, 661-667 (2004).

(56) References Cited

OTHER PUBLICATIONS

Stanisz, G. J. et al. Gd-DTPA relaxivity depends on macromolecular content. Magn. Reson. Med. 44, 665-667 (2000).
Taheri, S., et al. Quantitative measurement of blood-brain barrier permeability in human using dynamic contrast-enhanced MRI with fast T1 mapping. Magn. Reson. Med. 65, 1036-1042 (2011).
Towner, R. A. et al. In vivo detection of c-Met expression in a rat C6 glioma model. J. Cell. Mol. Med. 12, 174-186 (2008).
Wood, M. L. et al. Proton relaxation enhancement. J. Magn. Reson. Imaging 3, 149-156 (1993).
Ye, H. et al. Accelerating magnetic resonance fingerprinting (MRF) using t-blipped simultaneous multislice (SMS) acquisition. Magn. Reson. Med. 75, 2078-2085 (2016).
Zhou, Z. et al. MRI detection of breast cancer micrometastases with a fibronectin-targeting contrast agent. Nat. Commun. 6, 7984; doi:10.1038/ncomms8984 (2015).
Zhou, Z., et al. A targeted nanoglobular contrast agent from host-guest self-assembly for MR cancer molecular imaging. Biomaterials 85, 168-179 (2016).
De Haas, MH et al. Rapid Simultaneous Detection of Multiple Contrast Agents Using Magnetic Resonance Fingerprinting. Proceedings of the International Society for Magnetic Resonance in Medicine, vol. 24, 1572, Apr. 22, 2016.

\* cited by examiner

SYSTEM AND METHOD FOR DYNAMIC MULTIPLE CONTRAST ENHANCED, MAGNETIC RESONANCE FINGERPRINTING (DMCE-MRF)

CROSS-REFERENCE TO RELATED APPLICATIONS

This application represents the U.S. National Stage Entry of International Application PCT/US2018/026580, filed Apr. 6, 2018, which claims the benefit of, and claims priority to U.S. Provisional Application 62/482,755, filed Apr. 7, 2017. Each of the preceding applications is hereby incorporated by reference in its entirety for all purposes.

STATEMENT REGARDING FEDERALLY SPONSORED RESEARCH

This invention was made with government support under R01 DK085099 and R21 HL130839 awarded by the National Institutes of Health. The government has certain rights in the invention.

BACKGROUND

Conventional magnetic resonance imaging ("MRI") pulse sequences include repetitive similar preparation phases, waiting phases, and acquisition phases that serially produce signals from which images can be made. The preparation phase determines when a signal can be acquired and determines the properties of the acquired signal. For example, a first pulse sequence may produce a T1-weighted signal at a first echo time ("TE"), while a second pulse sequence may produce a T2-weighted signal at a second TE. These conventional pulse sequences typically provide qualitative results where data are acquired with various weightings or contrasts that highlight a particular parameter (e.g., T1 relaxation, T2 relaxation).

When magnetic resonance ("MR") images are generated, they may be viewed by a radiologist and/or surgeon who interprets the qualitative images for specific disease signatures. The radiologist may examine multiple image types (e.g., T1-weighted, T2-weighted) acquired in multiple imaging planes to make a diagnosis. The radiologist or other individual examining the qualitative images may need particular skill to be able to assess changes from session to session, from machine to machine, and from machine configuration to machine configuration.

Magnetic Resonance Imaging (MRI) provides physiological/molecular evaluations of numerous diseases including cancer, diabetes, cardiovascular diseases, and neurologic diseases. The overall utility of MRI is grounded in its ability to generate image sets with selectable soft tissue contrasts to detect pathophysiologic conditions through both endogenous soft tissue contrasts (e.g., T1, T2, diffusion, perfusion, chemical exchange saturation transfer (CEST)), as well as injectable MRI contrast agents (e.g., gadolinium chelates, paramagnetic iron containing compounds, CEST agents). However, a key limitation for current clinical MRI approaches is that MRI images are typically constrained to providing qualitative, diagnostic images that require subjective image interpretation. In recent years, a significant effort has been made to establish quantitative MRI techniques for both clinical and preclinical MRI studies with the goal of providing objective assessments that can be used to provide more sensitive and specific assessments of disease staging, progression, and therapeutic efficacy. When combined with molecular imaging platforms, these quantitative MRI techniques can shift the paradigm of clinical MRI from detecting late-stage structural changes to unraveling early-stage physiological/cellular changes underlying the disease development. Enabling this transition requires the development of highly-sensitive cellular/molecular MRI contrast agents as well as a robust quantitative MRI methods to detect these agents in vivo.

Over the past decade numerous investigators have developed a broad range of highly-sensitive MRI contrast agents that can be: 1) targeted to specific disease biomarkers such as peptides, cell-surface receptors, or other molecular constructs; 2) are ingested by or loaded into stem cells, macrophages, and other cells to track cell migration and immune cell activation; or 3) can provide a mechanism for targeted drug delivery with reduced systemic toxicity. These molecular MRI contrast agents are typically constructed from paramagnetic elements (e.g., gadolinium) that reduce the local T1 and T2 magnetic relaxation times of tissue. However, each paramagnetic MRI contrast agent alters both the T1 and T2 relaxation times thereby limiting these molecular MRI studies to one contrast agent at a time.

The ability to detect two or more MRI contrast agents simultaneously would provide the ability to directly compare contrast information resulting from the different contrast agents without registration errors and the like. The simultaneous detection of multiple MRI contrast agents would also provide the opportunity to delineate two separate cellular/molecular events in vivo. Currently, simultaneous multi-agent imaging capability is only available through optical imaging (i.e., multi-color fluorescence), multi-modality imaging systems (e.g., PET-MR), or multi-nuclear MRI imaging (e.g., fluorine-19).

Currently, contrast-enhanced MRI (CE-MRI) imaging studies are a hallmark for both a wide variety of clinical and preclinical imaging applications of many diseases including cancer, stroke, cardiovascular disease, vascular diseases, neurodegenerative diseases, as well as chronic diseases of the kidney, liver, and pancreas. These CE-MRI studies typically involve the intra-venous injection of a MRI contrast agent (e.g., gadolinium chelates, iron oxides) that simultaneously alter both T1 and T2 relaxation times of tissues through well-established concentration-dependent linear relationships shown in Equations 1A and 1B:

$$1/T1 = 1/T1_o + r1_A \times [A] \qquad (1A);$$

$$1/T2 = 1/T2_o + r2_A \times [A] \qquad (1B);$$

where [A] is the concentration of imaging agent A; $T1_o/T2_o$ are the pre-contrast T1 and T2 relaxation times of the tissue; T1/T2 are the post-contrast T1 and T2 relaxation times; and $r1_A$ and $r2_A$ are the relaxivities of the MRI contrast agent A. An individual MRI contrast agent is typically more sensitive to a particular relaxation parameter (i.e., Gd chelates are typically used for enhancement in T1-weighted imaging acquisitions). Therefore, knowing $r1_A$ and measuring the T1 relaxation time dynamically (pre and post-contrast) can provide a quantitative in vivo MRI assessment of the concentration of the imaging agent. As shown in FIGS. 1A, 1B, and 1C, this can be used to compare the retention of peptide-targeted imaging contrast agents in vivo. FIGS. 1A, 1B, and 1C show mean tumor normalized T1 values following intravenous administration of Optimark™, scrambled-Gd, or PTPµ-Gd (SBK2) contrast agents in cohorts of athymic mice bearing glioma flank tumors. Note the sustained decrease in normalized T1 for PTPµ-Gd due to agent clearance between the non-specific agents compared to PTPµ-Gd, which showed the highest retention. FIG. 1A shows mean tumor normalized T1 values. FIG. 1B shows the percent change in T1 was determined between 15 and 60 min post-injection to examine the rate of agent clearance. The PTPµ-Gd recovery was significantly different than both Optimark™ and scrambled-Gd. FIG. 1C shows LN-229 intracranial tumors are labeled with a 0.1 mmol/kg PTPµ-Gd probe.

Note that in this study, as for all prior MRI studies, the comparison of the targeted and control agents are performed separately at different times and normally in different animals. This is an important consideration as different animals show differential phenotypes, tumor growth, and the like and the different timepoints also have the potential to bias the results. It is also important to note that disease typically exhibits temporal and spatial heterogeneity in individuals, especially in human disease, making the analyses shown in FIG. 1 even more problematic. Therefore, there is a need for the capability to detect these two agents (molecular and control) separately and simultaneously in the same animal (or human patient).

Detection of multiple MRI contrast agents can be achieved using MR agents with different MRI-observable nuclei (e.g., $^1$H and $^{19}$F) where the multinuclear MRI acquisitions are interleaved. Unfortunately, detecting non-proton-based contrast agents with traditional MRI imaging techniques is time-consuming and suffers from significant reductions in sensitivity. Multinuclear MRI capabilities adds significant cost for specialized MRI hardware, such as special RF coils that are tuned to each nuclei. Such specialized MRI hardware and the software to operate the MRI system with specialized hardware in this manner are generally not available on a large majority of modern human MRI scanners. As such, attempts to use multiple MRI contrast agents that are imaged using traditional MRI techniques are cumbersome and clinically impractical.

A second option to detecting multiple contrast agents in vivo would be using two $^1$H MRI contrast agents that have different relaxivities. Unfortunately, a key limitation in all such contrast-enhanced studies relying on traditional MRI imaging techniques is that only one proton-based contrast agent can be detected at a time because all agents have an impact on both T1 and T2 relaxation times as shown in Equations 1A and 1B. Thus, attempting to use two $^1$H MRI contrast agents at the same time results in both contrast agents influencing the contrast mechanisms (T1 and T2) such that individual influence of one of the two $^1$H MRI contrast agents cannot be discerned. That is, the MRI data reflects a combination of the two $^1$H MRI contrast agents, effectively reducing the information to a single, combined contrast agent and undermining the purpose of attempting to use two $^1$H MRI contrast agents.

Therefore, a need persists to enable clinicians to acquire information from subjects that could be provided by using multiple dynamic contrast-enhanced studies, but without the expense and impracticality of specialized hardware and/or performing multiple independent studies, each of which can impart registration and motion issues, not to mention the time-consuming and cumbersome nature of performing multiple contrast-enhanced studies with a single patient in series (including the inherent time needed to allow a first contrast agent to wash out before beginning a second study).

SUMMARY OF THE DISCLOSURE

The present disclosure addresses the aforementioned drawbacks by providing systems and methods for dynamic, multiple, contrast-enhanced imaging studies of a patient using magnetic resonance fingerprinting (MRF). That is, the present disclosure provides systems and methods to perform dynamic, multi-contrast-enhanced MRF (DMCE-MRF) or dynamic, dual-contrast-enhanced MRF (DDCE-MRF). As such, multiple molecular MRI contrast agents can be used to target to a specific tissue, molecule, or cell during an imaging study. These contrast agents can also be molecular sensors to detect specific physiology and pathophysiologic conditions (e.g., pH). The ability to detect the corresponding control agent at the same time as the molecular agent allows the molecular information to be more thoroughly distinguished from the background physiology (e.g., vasculature).

In accordance with one aspect of the disclosure, the present disclosure provides a method of dynamic, multi-contrast-enhanced MRF. The method can include acquiring, with a magnetic resonance imaging (MRI) system using a series of variable sequence blocks that cause one or more resonance species in a region of interest (ROI) of a subject having received a dose of two or more contrast agents having at least two different relaxivities to simultaneously produce individual magnetic resonance signals, the simultaneously produced individual magnetic resonance signals as MRF signal evolutions. The method can also include comparing, using a computer system, the acquired MRF signal evolutions to a dictionary of signal evolutions to determine quantitative values for two or more parameters of the one or more resonant species based, at least in part, on matching the acquired MRF signal evolutions to a set of known signal evolutions stored in the dictionary, wherein the two or more parameters include at least a T1 relaxation time and a T2 relaxation time. The method can further include determining concentrations of the two or more contrast agents, using the computer system and a computer model that relates the different relaxivities, the T1 relaxation time, the T2 relaxation time, and concentrations of the two or more contrast agents. The method can also include producing an image depicting the ROI, at least in part, on the concentrations of the two or more contrast agents.

In accordance with another aspect of the disclosure, a system is provided that includes a magnet system configured to generate a polarizing magnetic field about at least a portion of a subject, a magnetic gradient system including a plurality of magnetic gradient coils configured to apply at least one magnetic gradient field to the polarizing magnetic field, and a radio frequency (RF) system configured to apply an RF field to the subject and to receive magnetic resonance signals from the subject using a coil array. The system also includes a computer system programmed to control the magnetic gradient system and the RF system to perform a series of variable sequence blocks that cause one or more resonance species in a region of interest (ROI) of a subject having received a dose of two or more contrast agents having at least two different relaxivities to simultaneously produce individual magnetic resonance signals to acquire the simultaneously produced individual magnetic resonance signals as MRF signal evolutions. The computer system is also programmed to compare the acquired MRF signal evolutions to a dictionary of signal evolutions to determine quantitative values for two or more parameters of the one or more resonant species based, at least in part, on matching the acquired MRF signal evolutions to a set of known signal evolutions stored in the dictionary, wherein the two or more parameters include at least a T1 relaxation time and a T2 relaxation time. The computer system is further configured to determine concentrations of the two or more contrast agents, using a model that relates the different relaxivities, the T1 relaxation time, the T2 relaxation time, and the concentrations of the two or more contrast agents. The system also includes a display configured to display at least one image of the ROI showing the concentrations of the two or more contrast agents.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Figure 1B:
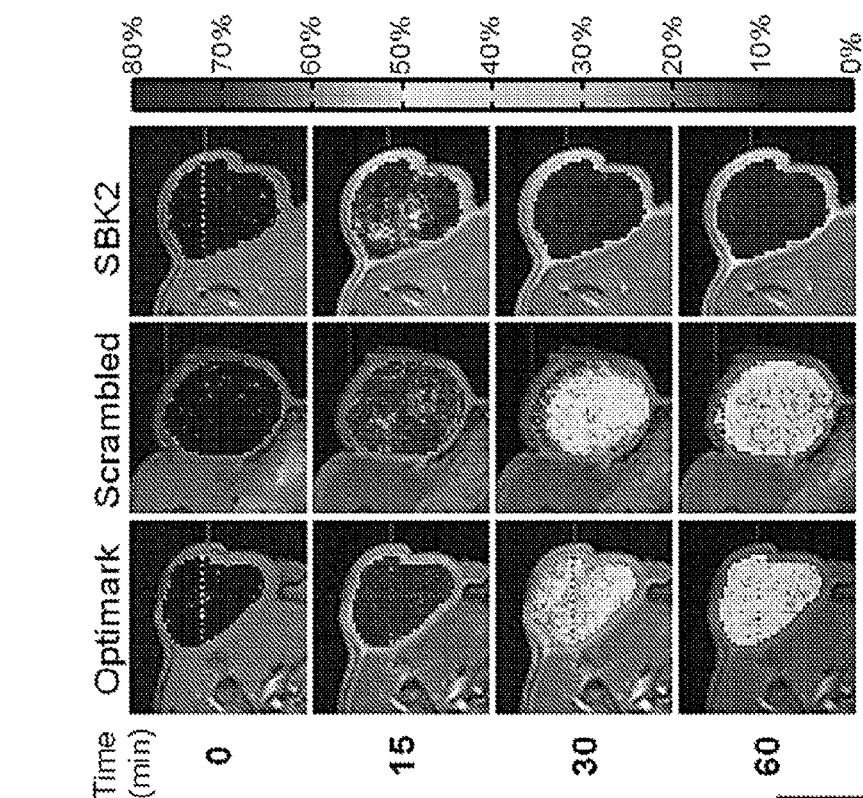
FIG. 1B is a series of images showing percent change in T1 values to examine rates of agent clearance.
Figure 1A:
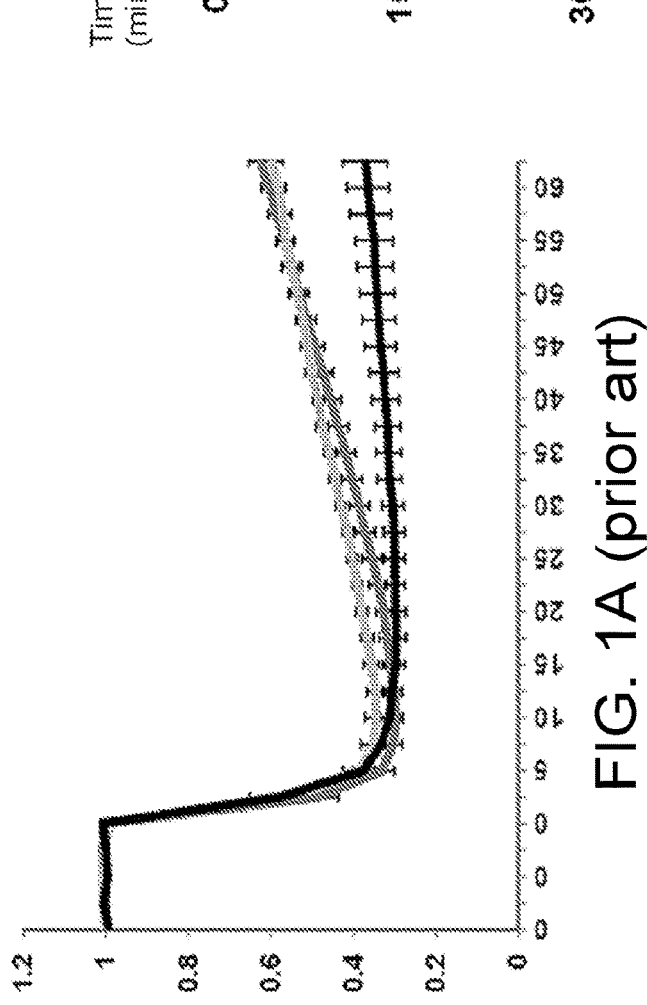
FIG. 1A is a plot of mean tumor normalized T1 values.
Figure 1C:
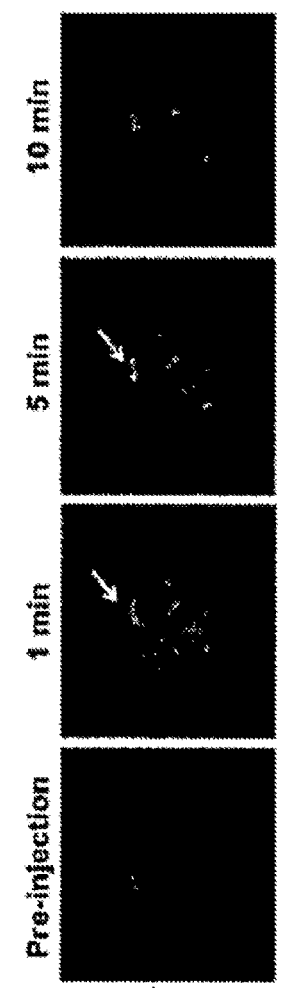
FIG. 1C is a series of images showing labeled intracranial tumors.
Figure 2:
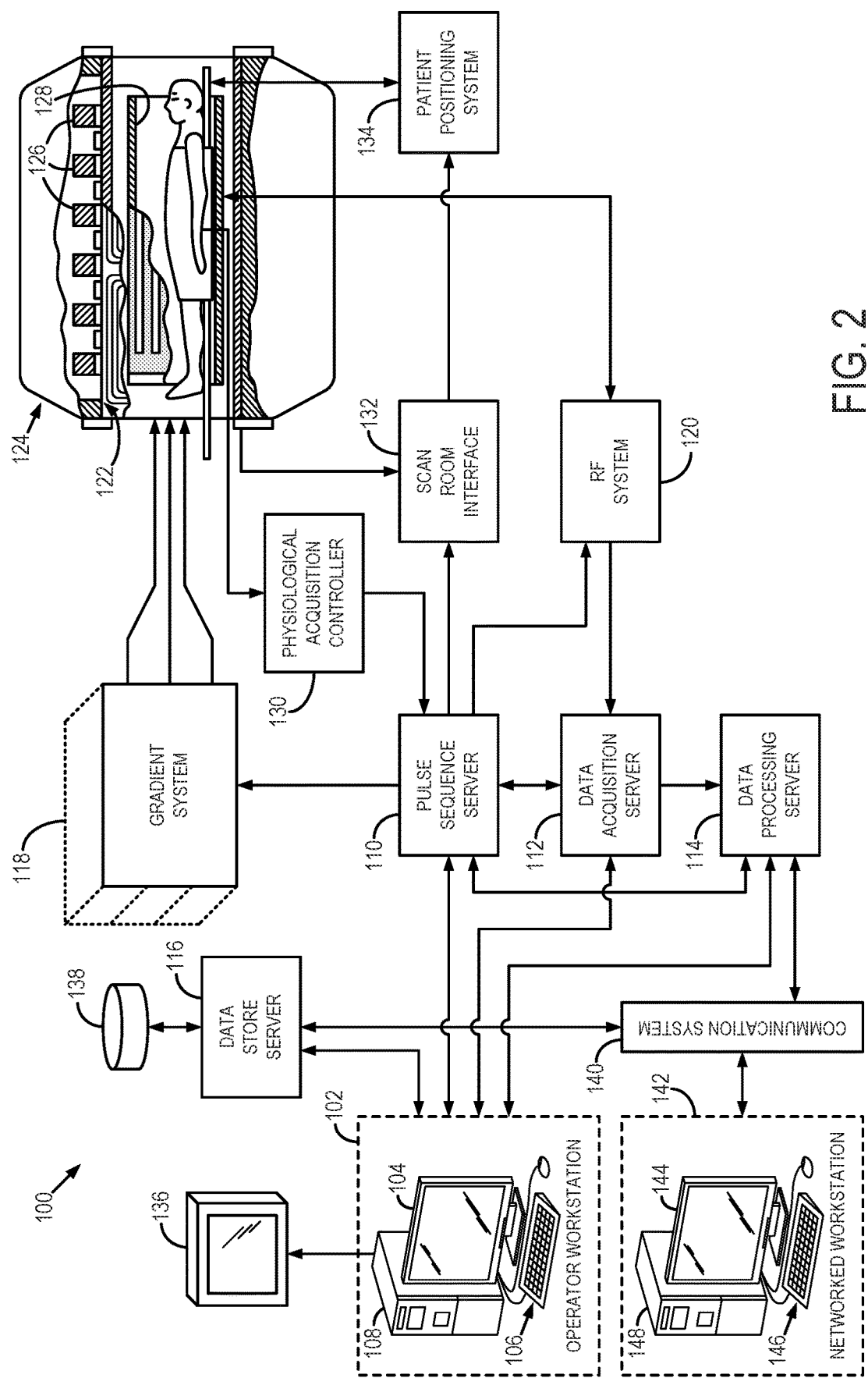
FIG. 2 is a block diagram of a non-limiting example of magnetic resonance imaging ("MRI") system that can implement the methods described in the present disclosure.

Referring particularly now to FIG. 2, an example of an MRI system 100 that can implement the methods described here is illustrated. The MRI system 100 includes an operator workstation 102 that may include a display 104, one or more input devices 106 (e.g., a keyboard, a mouse), and a processor 108. The processor 108 may include a commercially available programmable machine running a commercially available operating system. The operator workstation 102 provides an operator interface that facilitates entering scan parameters into the MRI system 100. The operator workstation 102 may be coupled to different servers, including, for example, a pulse sequence server 110, a data acquisition server 112, a data processing server 114, and a data store server 116. The operator workstation 102 and the servers 110, 112, 114, and 116 may be connected via a communication system 140, which may include wired or wireless network connections.

The pulse sequence server 110 functions in response to instructions provided by the operator workstation 102 to operate a gradient system 118 and a radiofrequency ("RF") system 120. Gradient waveforms for performing a prescribed scan are produced and applied to the gradient system 118, which then excites gradient coils in an assembly 122 to produce the magnetic field gradients $G_x$, $G_y$, and $G_z$ that are used for spatially encoding magnetic resonance signals. The gradient coil assembly 122 forms part of a magnet assembly 124 that includes a polarizing magnet 126 and a whole-body RF coil 128.

RF waveforms are applied by the RF system 120 to the RF coil 128, or a separate local coil to perform the prescribed magnetic resonance pulse sequence. Responsive magnetic resonance signals detected by the RF coil 128, or a separate local coil, are received by the RF system 120. The responsive magnetic resonance signals may be amplified, demodulated, filtered, and digitized under direction of commands produced by the pulse sequence server 110. The RF system 120 includes an RF transmitter for producing a wide variety of RF pulses used in MRI pulse sequences. The RF transmitter is responsive to the prescribed scan and direction from the pulse sequence server 110 to produce RF pulses of the desired frequency, phase, and pulse amplitude waveform. The generated RF pulses may be applied to the whole-body RF coil 128 or to one or more local coils or coil arrays.

The RF system 120 also includes one or more RF receiver channels. An RF receiver channel includes an RF preamplifier that amplifies the magnetic resonance signal received by the coil 128 to which it is connected, and a detector that detects and digitizes the I and Q quadrature components of the received magnetic resonance signal. The magnitude of the received magnetic resonance signal may, therefore, be determined at a sampled point by the square root of the sum of the squares of the I and Q components:

$$M=\sqrt{I^2+Q^2} \qquad (4);$$

and the phase of the received magnetic resonance signal may also be determined according to the following relationship:

$$\varphi = \tan^{-1}\left(\frac{Q}{I}\right). \qquad (5)$$

The pulse sequence server 110 may receive patient data from a physiological acquisition controller 130. By way of example, the physiological acquisition controller 130 may receive signals from a number of different sensors connected to the patient, including electrocardiograph ("ECG") signals from electrodes, or respiratory signals from a respiratory bellows or other respiratory monitoring devices. These signals may be used by the pulse sequence server 110 to synchronize, or "gate," the performance of the scan with the subject's heart beat or respiration.

The pulse sequence server 110 may also connect to a scan room interface circuit 132 that receives signals from various sensors associated with the condition of the patient and the magnet system. Through the scan room interface circuit 132, a patient positioning system 134 can receive commands to move the patient to desired positions during the scan.

The digitized magnetic resonance signal samples produced by the RF system 120 are received by the data acquisition server 112. The data acquisition server 112 operates in response to instructions downloaded from the operator workstation 102 to receive the real-time magnetic resonance data and provide buffer storage, so that data is not lost by data overrun. In some scans, the data acquisition server 112 passes the acquired magnetic resonance data to the data processor server 114. In scans that require information derived from acquired magnetic resonance data to control the further performance of the scan, the data acquisition server 112 may be programmed to produce such information and convey it to the pulse sequence server 110. For example, during pre-scans, magnetic resonance data may be acquired and used to calibrate the pulse sequence performed by the pulse sequence server 110. As another example, navigator signals may be acquired and used to adjust the operating parameters of the RF system 120 or the gradient system 118, or to control the view order in which k-space is sampled. In still another example, the data acquisition server 112 may also process magnetic resonance signals used to detect the arrival of a contrast agent in a magnetic resonance angiography ("MRA") scan. For example, the data acquisition server 112 may acquire magnetic resonance data and processes it in real-time to produce information that is used to control the scan.

The data processing server 114 receives magnetic resonance data from the data acquisition server 112 and processes the magnetic resonance data in accordance with instructions provided by the operator workstation 102. Such processing may include, for example, reconstructing two-dimensional or three-dimensional images by performing a Fourier transformation of raw k-space data, performing other image reconstruction algorithms (e.g., iterative or backprojection reconstruction algorithms), applying filters to raw k-space data or to reconstructed images, generating functional magnetic resonance images, or calculating motion or flow images.

Images reconstructed by the data processing server 114 are conveyed back to the operator workstation 102 for storage. Real-time images may be stored in a data base memory cache, from which they may be output to operator display 102 or a display 136. Batch mode images or selected real time images may be stored in a host database on disc storage 138. When such images have been reconstructed and transferred to storage, the data processing server 114 may notify the data store server 116 on the operator workstation 102. The operator workstation 102 may be used by an operator to archive the images, produce films, or send the images via a network to other facilities.

The MRI system 100 may also include one or more networked workstations 142. For example, a networked workstation 142 may include a display 144, one or more input devices 146 (e.g., a keyboard, a mouse), and a processor 148. The networked workstation 142 may be located within the same facility as the operator workstation 102, or in a different facility, such as a different healthcare institution or clinic.

The networked workstation 142 may gain remote access to the data processing server 114 or data store server 116 via the communication system 140. Accordingly, multiple networked workstations 142 may have access to the data processing server 114 and the data store server 116. In this manner, magnetic resonance data, reconstructed images, or other data may be exchanged between the data processing server 114 or the data store server 116 and the networked workstations 142, such that the data or images may be remotely processed by a networked workstation 142.

As will be described, the present disclosure recognizes that magnetic resonance fingerprinting ("MRF") can be used to perform dynamic, multi-contrast-enhanced studies to overcome the shortcomings of attempts to perform dynamic, dual-contrast-enhanced studies using traditional MRI techniques. Furthermore, dynamic, multi-contrast-enhanced MRF in accordance with the present disclosure can be performed using an MRI or NMR system, such as described above with respect to FIG. 2, without the need for expensive, specialized hardware or the like. Thus, dynamic, multi-contrast-enhanced MRF can be delivered clinically.

MRF is a technique that facilitates mapping of tissue or other material properties based on random or pseudorandom measurements of the subject or object being imaged. Characterizing tissue species using nuclear magnetic resonance ("NMR") can include identifying different properties of a resonant species (e.g., T1 spin-lattice relaxation, T2 spin-spin relaxation, proton density). Other properties like tissue types and super-position of attributes can also be identified using NMR signals. These properties and others may be identified simultaneously using MRF, which is described, as one example, by D. Ma, et al., in "Magnetic Resonance Fingerprinting," Nature, 2013; 495(7440):187-192.

In particular, MRF can be conceptualized as employing a series of varied "sequence blocks" that simultaneously produce different signal evolutions in different "resonant species" to which the RF is applied. The term "resonant species," as used herein, refers to a material, such as water, fat, bone, muscle, soft tissue, and the like, that can be made to resonate using NMR. By way of illustration, when radio frequency ("RF") energy is applied to a volume that has both bone and muscle tissue, then both the bone and muscle tissue will produce a NMR signal; however, the "bone signal" represents a first resonant species and the "muscle signal" represents a second resonant species, and thus the two signals will be different. These different signals from different species can be collected simultaneously over a period of time to collect an overall "signal evolution" for the volume.

The random or pseudorandom measurements obtained in MRF techniques are achieved by varying the acquisition parameters from one repetition time ("TR") period to the next, which creates a time series of signals with varying contrast. Examples of acquisition parameters that can be varied include flip angle ("FA"), RF pulse phase, TR, echo time ("TE"), and sampling patterns, such as by modifying one or more readout encoding gradients. The acquisition parameters are varied in a random manner, pseudorandom manner, or other manner that results in signals from different materials or tissues to be spatially incoherent, temporally incoherent, or both. For example, in some instances, the acquisition parameters can be varied according to a non-random or non-pseudorandom pattern that otherwise results in signals from different materials or tissues to be spatially incoherent, temporally incoherent, or both.

From these measurements, which as mentioned above may be random or pseudorandom, or may contain signals from different materials or tissues that are spatially incoherent, temporally incoherent, or both, MRF processes can be designed to map any of a wide variety of parameters. Examples of such parameters that can be mapped may include, but are not limited to, longitudinal relaxation time ($T_1$), transverse relaxation time ($T_2$), main or static magnetic field map ($B_0$), and proton density ($\varphi$. MRF is generally described in U.S. Pat. No. 8,723,518 and Published U.S. Patent Application No. 2015/0301141, each of which is incorporated herein by reference in its entirety.

The data acquired with MRF techniques are compared with a dictionary of signal models, or templates, that have been generated for different acquisition parameters from magnetic resonance signal models, such as Bloch equation-based physics simulations. This comparison allows estimation of the physical parameters, such as those mentioned above. As an example, the comparison of the acquired signals to a dictionary can be performed using any suitable matching or pattern recognition technique. The parameters for the tissue or other material in a given voxel are estimated to be the values that provide the best signal template matching. For instance, the comparison of the acquired data with the dictionary can result in the selection of a signal vector, which may constitute a weighted combination of signal vectors, from the dictionary that best corresponds to the observed signal evolution. The selected signal vector includes values for multiple different quantitative parameters, which can be extracted from the selected signal vector and used to generate the relevant quantitative parameter maps.

The stored signals and information derived from reference signal evolutions may be associated with a potentially very large data space. The data space for signal evolutions can be partially described by:

$$SE = \sum_{s=1}^{N_S} \prod_{i=1}^{N_A} \sum_{j=1}^{N_{RF}} R_i(\alpha) R_{RF_{ij}}(\alpha, \phi) R(G) E_i(T_1, T_2, D) M_0; \quad (2)$$

where SE is a signal evolution; $N_S$ is a number of spins; $N_A$ is a number of sequence blocks; $N_{RF}$ is a number of RF pulses in a sequence block; $\alpha$ is a flip angle; $\phi$ is a phase angle; $R_i(\alpha)$ is a rotation due to off resonance; $R_{RF_{ij}}(\alpha,\phi)$ is a rotation due to RF differences; $R(G)$ is a rotation due to a magnetic field gradient; $T_1$ is a longitudinal, or spin-lattice, relaxation time; $T_2$ is a transverse, or spin-spin, relaxation time; D is diffusion relaxation; $E_i(T_1, T_2, D)$ is a signal decay due to relaxation differences; and $M_0$ is the magnetization in the default or natural alignment to which spins align when placed in the main magnetic field.

While $E_i(T_1,T_2,D)$ is provided as an example, in different situations, the decay term, $E_i(T_1,T_2,D)$, may also include additional terms, $E_i(T_1,T_2,D,K)$ or may include fewer terms, such as by not including the diffusion relaxation, as $E_i(T_1, T_2)$ or $E_i(T_1,T_2,K)$. Also, the summation on "j" could be replace by a product on "j".

The dictionary may store signals described by, $$S_i = R_i E_i(S_{i-1}) \quad (3);$$

where $S_0$ is the default, or equilibrium, magnetization; $S_i$ is a vector that represents the different components of magnetization, $M_x$, $M_y$, and $M_z$ during the $i^{th}$ acquisition block; $R_i$ is a combination of rotational effects that occur during the $i^{th}$ acquisition block; and $E_i$ is a combination of effects that alter the amount of magnetization in the different states for the $i^{th}$ acquisition block. In this situation, the signal at the $i^{th}$ acquisition block is a function of the previous signal at acquisition block (i.e., the $(i-1)^{th}$ acquisition block). Additionally or alternatively, the dictionary may store signals as a function of the current relaxation and rotation effects and of previous acquisitions. Additionally or alternatively, the dictionary may store signals such that voxels have multiple resonant species or spins, and the effects may be different for every spin within a voxel. Further still, the dictionary may store signals such that voxels may have multiple resonant species or spins, and the effects may be different for spins within a voxel, and thus the signal may be a function of the effects and the previous acquisition blocks.

Figure 3:
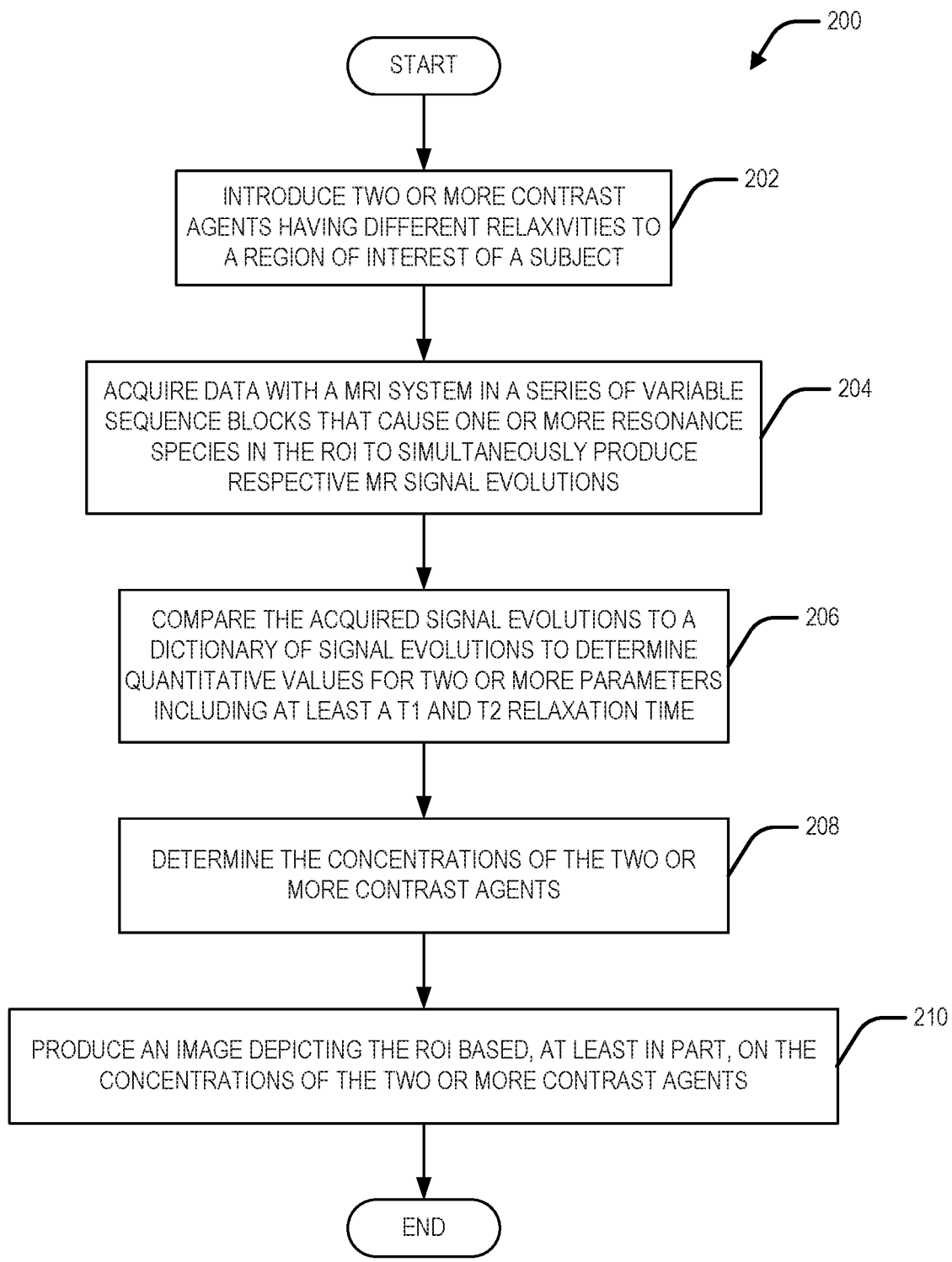
FIG. 3 is a flowchart illustrating a method in accordance with the present disclosure.

Referring to FIG. 3, the present disclosure provides a method 200 of DMCE-MRF. At process block 202, the method 200 includes performing a dynamic MRF data acquisition repeated over multiple timepoints, such as described above, including acquiring data with a magnetic resonance imaging (MRI) system in a series of variable sequence blocks that cause one or more resonance species in the ROI to simultaneously produce respective MRF signal evolutions. At process block 204, the method 200 includes introducing two or more contrast agents to a region of interest (ROI) of a subject, the two or more contrast agents having different relaxivities. At process block 206, the method 200 includes comparing the acquired signal evolutions at each timepoint to a dictionary of signal evolutions to determine quantitative values for two or more parameters of the resonant based species based, at least in part, on matching the separated magnetic resonance data to a set of known signal evolutions stored in the dictionary. The two or more parameters may include at least a T1 relaxation time and a T2 relaxation time. At process block 208, the method 200 includes determining, using a model, such as using a computer or computer system and a computer model, that relate the different relaxivities, the T1 relaxation time, the T2 relaxation time, and concentrations of the two or more contrast agents. At process block 210, the method 200 includes producing an image depicting the ROI based, at least in part, on the concentrations of the two or more contrast agents.

As further described above, MRF (MRF, Nature 2013) is a nuclear magnetic resonance (NMR) technique that has been shown in human imaging studies to simultaneously generate quantitative maps. The MRF techniques use variation in the MRF acquisition parameters using a series of variable sequence blocks to elicit signal evolutions that can be examined a pattern-matching process to generate robust quantitative maps, including quantitative T1 and T2 estimates with inherent resistant to motion artifacts.

With this in mind, the above-described process has been implemented using a fast imaging with steady-state free precession (FISP) acquisition kernel to control banding artifacts from True FISP MRI acquisitions that are prevalent on high field MRI scanners. Similar to previous clinical MRF studies, results showed that undersampled spiral trajectories for sampling k-space can be used to obtain dynamic MRF-based T1 and T2 relaxation times estimates in animal models.

Using the methods described in the present disclosure, T1 and T2 relaxation times can be dynamically and simultaneously acquired, which enables the detection of two different proton MRI contrast agents (i.e., having different relaxivities, r1 and r2) at the same time. For molecular imaging studies, this adaptable dynamic dual contrast enhanced MRF (DDCE-MRF) approach provides the ability to specifically assess two different tissue compartments or molecular targets in vivo simultaneously using a single MRF acquisition. In a similar fashion, the multiple MRI assessments of T1 and T2 relaxation times allows for the quantification of in vivo assessments of correlation times for specific imaging agents.

Figure 4:
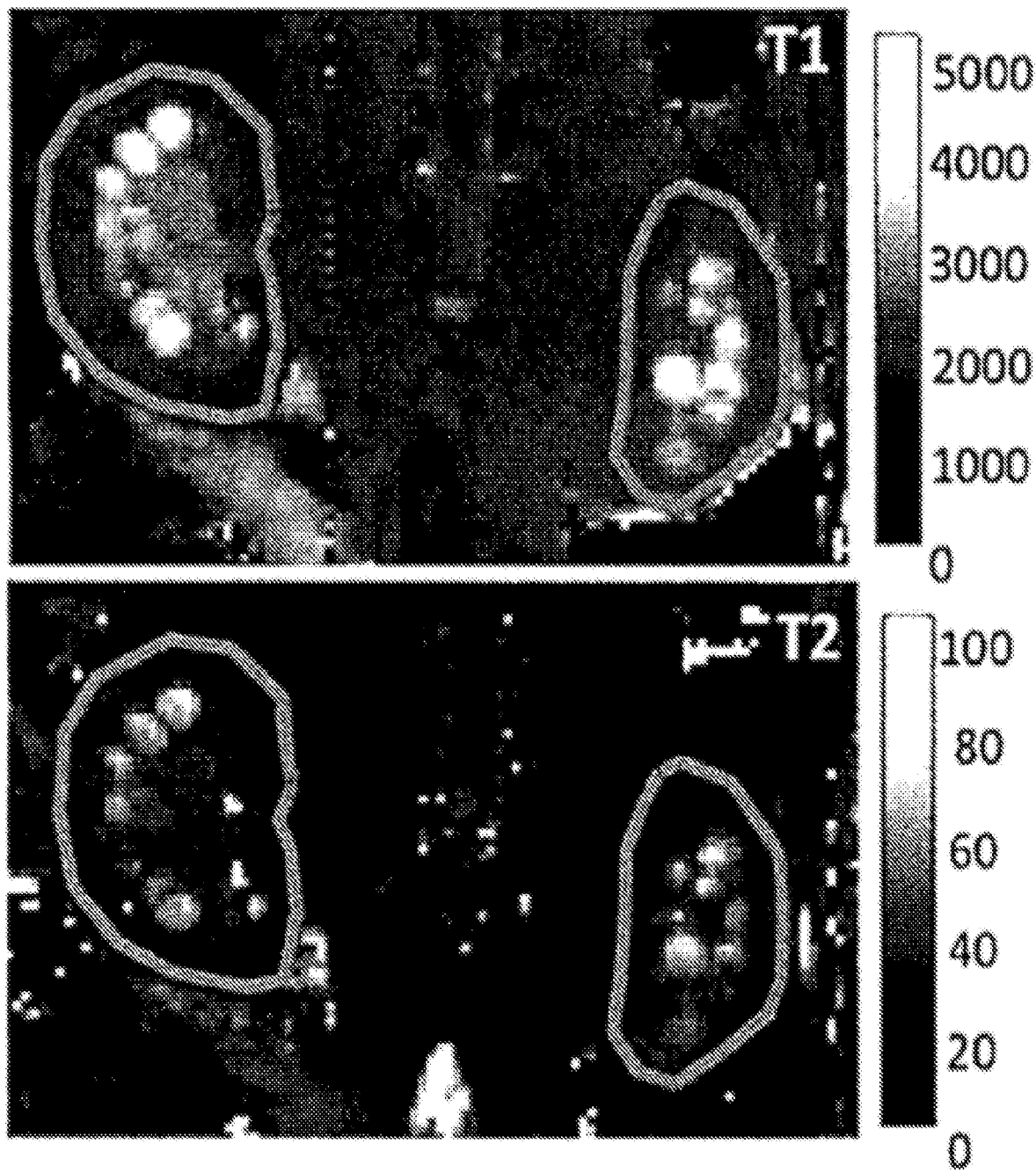
FIG. 4 is a pair of images showing MRF-based T1 and T2 measurements of PCK rat model of ARPKD.

In one non-limiting example of an implementation of the above-described technique, an MRF acquisition such as described above was performed to rapidly (~10 seconds/imaging slice) and simultaneously generate multiple imaging parameters, including T1 and T2 relaxation time maps. The MRF methodology dynamically acquired ~1000 images of the same imaging slice in ~10 seconds. This set of 1000 images had time-varying tissue contrast forming signal evolutions that were elicited by the variable sequence blocks with varied MRF acquisition parameters. Within those time-varying tissue contrast were varying T1 and T2 values for the particular tissue. Instead of Fourier transforms used in conventional MRI, the MRF methodology used a pre-calculated dictionary of known signal evolutions to match the acquired signal evolution profiles for each image pixel to a "best-matching" profile in the MRF dictionary. In the original MRF publication (Nature, 2013), the MRF matching process was shown to be resistant to patient motion. In an example study, MRF results (T1 and T2 maps) were obtained in the PCK rat model of Autosomal Recessive Polycystic Kidney Disease (FIG. 4). Hyperintense cysts are visible in both the T1 and T2 maps as expected as cysts are known to have higher T1 and T2 values.

FIG. 4 shows MRF of PCK rat model of ARPKD. MRF-based T1 (top panel) and T2 (bottom panel) images of a 1-month old PCK rat are shown. The left and right kidneys are outlined in each map. Note the contrast between the cysts and renal parenchyma in both the T1 and T2 maps.

As described above, detection of multiple MRI contrast agents can be achieved using MR agents with different MRI-observable nuclei (e.g., $^1$H and $^{19}$F) where the multinuclear MRI acquisitions are interleaved. Unfortunately, detecting non-proton-based contrast agents with traditional MRI imaging techniques is time-consuming and suffers from significant reductions in sensitivity. Again, multinuclear MRI capabilities adds significant cost for specialized MRI hardware and are generally not available on a large majority of modern human MRI scanners. The systems and methods of the present disclosure can be performed using, for example, the system of FIG. 2, which does not include or require specialized RF coil systems tuned to each nuclei.

As also described above, a second option to detecting multiple contrast agents in vivo would be using two $^1$H MRI contrast agents that have different relaxivities. Unfortunately, as described above, a key limitation in all previous contrast-enhanced studies relying on traditional MRI imaging techniques is that only one proton-based contrast agent can be detected at a time because all agents have an impact on both T1 and T2 relaxation times, as shown in Equations 1A and 1B. If agents A and B are injected simultaneously, the impact of these agents could be modeled as shown in Equations 6A and 6B:

$$1/T1 = 1/T1_0 + r1_A \times [A] + r1_B \times [B] \quad (6A);$$

$$1/T2 = 1/T2_0 + r2_A \times [A] + r2_B \times [B] \quad (6B).$$

These equations may be valid within specific concentration limits: 1) low enough concentration to limit interactions and avoid T1/T2 saturation; 2) high enough concentration to be individually detected. These equations also assume minimal interaction between the two agents as these would be simultaneously injected as a mixture. Within these constraints, measuring both T1 and T2 relaxation times dynamically, as can be achieved using the systems and methods described herein, these two equations can be analytically solved for both [A] and [B]. As a result, studies the systems and methods of the present disclosure allow for simultaneously measuring both the targeted and untargeted control agents (as in FIG. 4). The approach can also be applied to two targets exploring different aspects of pathophysiology/disease progression. One option to perform multi-agent detection is to interleave T1 and T2 relaxometric assessments. However, if the quantitative T1 and T2 relaxometric assessments are not fast enough, then the local concentration of the contrast agent can change significantly between the T1 and T2 measurements, resulting in a temporal mismatch between the T1 and T2 relaxation time assessments. This temporal mismatch would then result in significant errors in the calculated estimates of the respective agent concentrations.

Figure 5:
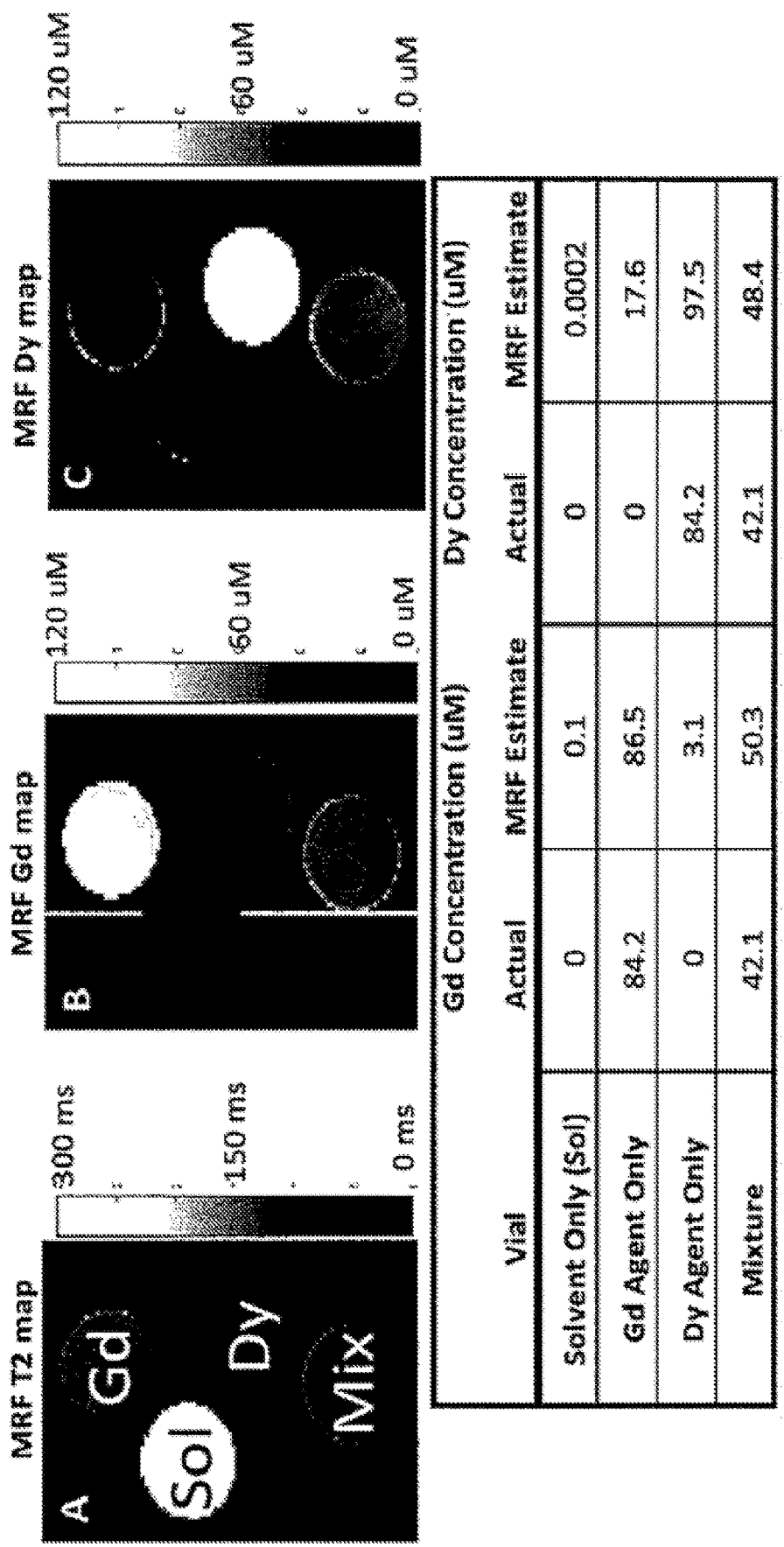
FIG. 5 is an initial in vitro MRF assessment of two different MRI contrast agents.

The systems and methods of the present disclosure overcome the issue presented by this temporal mismatch and associated errors by allowing for simultaneous and rapid assessment of T1 and T2 relaxation times. Specifically, FIG. 5 demonstrates the ability of the systems and methods of the present disclosure to simultaneously detect two different MRI contrast agents. To create this non-limiting example, four different vials were scanned with known concentrations of Gd-based and Dy-based MRI contrast agents. The four vials contained 1) solvent only (no contrast agents); 2) Gd-based agent only; 3) Dy-based agent only; and 4) a mixture of the two agents. For this initial in vitro study, the "gold-standard" spin echo MRI acquisitions were used to measure the T1 and T2 relaxation times of each vial within a 7T Bruker Biospec MRI scanner. T1 and T2 estimates form the gold-standard MRI acquisitions for the solvent and individual agents were used to calculate the relaxivities for the two agents at 300 MHz. Also, MRF-based T1 and T2 maps were then used to calculate separate Gd and Dy maps for the four vials. The mean Gd/Dy concentrations in each vial are shown in FIG. 5. Importantly, the maps show reasonable agreement with the actual concentrations for this initial implementation. Gold-standard assessments illustrates that errors for using this mixture model of relaxation can be constrained to be less than 5%. Thus, the present disclosure provides, for the first time, the ability to accurately detect two contrast agents simultaneously in vivo using DMCE-MRF.

Thus, FIG. 5 shows an initial in vitro MRF assessment of two different MRI contrast agents. Map A is an MRF-based T2 relaxation time map showing the different relaxation time for the individual and mixed Gd and Dy contrast agents as well as the solvent. Maps B and C respectively are the calculated Gd and Dy maps obtained from the MRF T1 and T2 assessments. MRF-based estimates of vial concentrations are shown in the Table in comparison to actual concentrations. Note the reasonable agreement for this initial test.

Notably, relative to Equations 1A and 1B, there is only one unknown value if $r1_A$ and $r1_B$ are predetermined. These relaxivities can be measured in vivo, ex vivo, and in vitro. Importantly, in vivo relaxivities are significantly different from in vitro values because the in vivo correlation times are altered through tissue-agent interactions. The ability of the systems and methods of the present disclosure to measure T1 and T2 simultaneously provides the ability to measure $r1_A$ and $r2_A$ efficiently in a variety of diseases. For example, a series of subjects can be injected with varying amounts of the contrast agent while dynamically acquiring the T1 and T2 maps of specific tissues of interest. The in vivo T1 and T2 assessments can be used to calculate the in vivo r1 and r2 relaxivities in the same subject (rather than two separate groups) to reduce the number of experiments and/or improved estimates.

The present disclosure has described one or more preferred embodiments, and it should be appreciated that many equivalents, alternatives, variations, and modifications, aside from those expressly stated, are possible and within the scope of the invention.

The invention claimed is:

1. A method of dynamic, contrast-enhanced, magnetic resonance fingerprinting (MRF), the method including steps comprising:
   a) acquiring, with a magnetic resonance imaging (MRI) system using a series of variable sequence blocks that cause one or more resonance species in a region of interest (ROI) of a subject having received a dose of two or more contrast agents having at least two different relaxivities to simultaneously produce individual magnetic resonance signals, the simultaneously produced individual magnetic resonance signals as MRF signal evolutions;
   b) comparing, using a computer system, the acquired MRF signal evolutions to a dictionary of signal evolutions to determine quantitative values for two or more parameters of the one or more resonant species based, at least in part, on matching the acquired MRF signal evolutions to a set of known signal evolutions stored in the dictionary, wherein the two or more parameters include at least a T1 relaxation time and a T2 relaxation time;

c) determining, using the computer system and a computer model that relates the different relaxivities, the T1 relaxation time, the T2 relaxation time, and concentrations of the two or more contrast agents, the concentrations of the two or more contrast agents;

d) producing an image depicting the ROI, at least in part, based on the concentrations of the two or more contrast agents; and wherein the computer model includes the form:

$$1/T1 = 1/T1_0 + r1_A \times [A] + r1_B \times [B] \text{ and } 1/T2 = 1/T2_0 + r2_A \times [A] + r2_B \times [B];$$

wherein $T1_0$ is a pre-contrast T1 relaxation value of tissue in the ROI, $T2_0$ is a pre-contrast T2 relaxation value of tissue in the ROI; T1 is a post-contrast T1 relaxation value of tissue in the ROI, T2 is a post-contrast T2 relaxation value; [A] is a concentration of a first of the two or more contrast agents; $r1_A$ is an r1 relaxivity of first of the two or more contrast agents; $r2_A$ is an r2 relaxivity of first of the two or more contrast agents; [B] is a concentration of a second of the two or more contrast agents; $r1_B$ is an r1 relaxivity of second of the two or more contrast agents; and $r2_B$ is a r2 relaxivity of second of the two or more contrast agents.

2. The method of claim 1 wherein the image indicates contrast attributable to two different tissue compartments in the ROI or two different molecular targets in the subject.

3. The method of claim 1 wherein step a) includes performing a fast imaging with steady-state free precession (FISP) acquisition kernel.

4. The method of claim 3 wherein performing the FISP acquisition kernel includes sampling k-space using spiral trajectories.

5. A system comprising:

a magnet system configured to generate a polarizing magnetic field about at least a portion of a subject;

a magnetic gradient system including a plurality of magnetic gradient coils configured to apply at least one magnetic gradient field to the polarizing magnetic field;

a radio frequency (RF) system configured to apply an RF field to the subject and to receive magnetic resonance signals from the subject using a coil array;

a computer system programmed to:

control the magnetic gradient system and the RF system to perform a series of variable sequence blocks that cause one or more resonance species in a region of interest (ROI) of a subject having received a dose of two or more contrast agents having at least two different relaxivities to simultaneously produce individual magnetic resonance signals to acquire the simultaneously produced individual magnetic resonance signals as MRF signal evolutions;

compare the acquired MRF signal evolutions to a dictionary of signal evolutions to determine quantitative values for two or more parameters of the one or more resonant species based, at least in part, on matching the acquired MRF signal evolutions to a set of known signal evolutions stored in the dictionary, wherein the two or more parameters include at least a T1 relaxation time and a T2 relaxation time;

determine, using a model that relates the different relaxivities, the T1 relaxation time, the T2 relaxation time, and concentrations of the two or more contrast agents, the concentrations of the two or more contrast agents;

a display configured to display at least one image of the ROI showing the concentrations of the two or more contrast agents; and wherein the computer model includes the form:

$$1/T1 = 1/T1_0 + r1_A \times [A] + r1_B \times [B] \text{ and } 1/T2 = 1/T2_0 + r2_A \times [A] + r2_B \times [B];$$

wherein $T1_0$ is a pre-contrast T1 relaxation value of tissue in the ROI, $T2_0$ is a pre-contrast T2 relaxation value of tissue in the ROI; T1 is a post-contrast T1 relaxation value of tissue in the ROI, T2 is a post-contrast T2 relaxation value; [A] is a concentration of a first of the two or more contrast agents; $r1_A$ is an r1 relaxivity of first of the two or more contrast agents; $r2_A$ is an r2 relaxivity of first of the two or more contrast agents; [B] is a concentration of a second of the two or more contrast agents; $r1_B$ is an r1 relaxivity of second of the two or more contrast agents; and $r2_B$ is a r2 relaxivity of second of the two or more contrast agents.

6. The system of claim 5 wherein the at least one image is generated by the computer system to indicate contrast attributable to two different tissue compartments in the ROI or two different molecular targets in the subject.

7. The system of claim 5 wherein the computer system is further configured to perform a fast imaging with steady-state free precession (FISP) acquisition kernel to acquire the signal evolutions.

8. The system of claim 7 wherein performing the FISP acquisition kernel includes sampling k-space using spiral trajectories.

* * * * *

UNITED STATES PATENT AND TRADEMARK OFFICE
CERTIFICATE OF CORRECTION

| | |
|---|---|
| PATENT NO. | : 11,442,127 B2 |
| APPLICATION NO. | : 16/603335 |
| DATED | : September 13, 2022 |
| INVENTOR(S) | : Chris Flask et al. |

It is certified that error appears in the above-identified patent and that said Letters Patent is hereby corrected as shown below:

In the Specification

Column 8, Line 47 "($\varphi$." should be --($\rho$)--.

Signed and Sealed this
Fifteenth Day of November, 2022

*Katherine Kelly Vidal*

Katherine Kelly Vidal
*Director of the United States Patent and Trademark Office*